US006284498B1

(12) United States Patent
Fouache et al.

(10) Patent No.: US 6,284,498 B1
(45) Date of Patent: *Sep. 4, 2001

(54) METHOD OF MANUFACTURING A MALTOSE-RICH SYRUP

(75) Inventors: Catherine Fouache, Sailly Labourse; Didier Delobeau, Merville; Bruno Quenon, Sailly sur la Lys, all of (FR)

(73) Assignee: Roquette Freres, Lestrem (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/160,136

(22) Filed: Sep. 25, 1998

(30) Foreign Application Priority Data

Sep. 26, 1997 (FR) .................................................. 97 12036

(51) Int. Cl.⁷ ........................................................ C12P 19/22
(52) U.S. Cl. .................................. 435/95; 435/96; 435/98; 435/99; 435/100
(58) Field of Search ................................. 435/100, 95, 96, 435/98, 99

(56) References Cited

U.S. PATENT DOCUMENTS

| | | |
|---|---|---|
| 3,708,396 | 1/1973 | Mitsuhashi et al. . |
| 4,294,623 | 10/1981 | Hidaka et al. . |
| 4,429,122 | 1/1984 | Zupancic . |
| 4,487,198 | 12/1984 | Miyake et al. . |
| 4,511,654 | 4/1985 | Rohrbach et al. . |
| 4,849,023 | 7/1989 | Devos et al. . |
| 5,141,859 | 8/1992 | Niimi et al. . |
| 5,356,808 | * 10/1994 | Purdue et al. .................... 435/254.2 |

FOREIGN PATENT DOCUMENTS

| | | |
|---|---|---|
| 0 231 729 | 8/1987 | (EP) . |
| 1.283.571 | 7/1972 | (GB) . |
| 49-55857 | * 5/1974 | (JP) . |
| WO 95.10627 | 4/1995 | (WO) . |

OTHER PUBLICATIONS

Takashi et al. Starch/Stärk 44(3):96–101, 1992.*
Chemical Abstracts 122(17):212462q, 1995.*
Chemical Abstracts 126(16):211237r, 1997.*
Jung K H et al: "production of high fructo–oligosaccharide syrup with two enzyme system of fructosylatransferase and glucose oxidase" Biotech. Letters 15(1):65–70 (1993).
Patent Abstracts of Japan (Kohjin Co Ltd), May 26, 1986, Abstract of JP 61104794.

* cited by examiner

Primary Examiner—Francisco Prats
(74) Attorney, Agent, or Firm—Henderson & Sturm LLP

(57) ABSTRACT

The invention relates to a method of manufacturing a maltose-rich syrup, comprising the successive stages consisting of:

(a) carrying out a liquefaction of a starch milk;

(b) carrying out a saccharification of the liquefied starch milk in the presence of a maltogenic α-amylase;

(c) continuing the saccharification of the liquefied starch milk in the presence of a β-amylase and at least one debranching enzyme chosen from the group consisting of pullulanases and isoamylases with a view to obtaining a syrup which is rich in maltose.

10 Claims, No Drawings

METHOD OF MANUFACTURING A MALTOSE-RICH SYRUP

The invention relates to a method of manufacturing a syrup which is rich in maltose. It relates equally to a method of manufacturing a syrup which is rich in maltitol from a maltose-rich syrup obtained by the method according to the present invention.

Methods allowing the production of maltose-rich syrups are already known. Amongst these methods it is possible to quote in particular the one described by HODGE and Coll. in "Cereal Chemistry" No 25, pages 19–30, January 1948, and which contains a stage of precipitation of limit-dextrins by alcohol solutions, and the one described by WOLFROM and THOMPSON in "Methods in carbohydrate chemistry", 1962, pages 334–335, and which includes a stage of repeated crystallisation of the octaacetate of maltose followed by the crystallisation of the maltose.

Other methods of manufacturing maltose-rich syrups have also been proposed comprising a stage of adsorption on charcoal of the dextrins (U.S. Pat. No. 4.194.623), a stage of chromatography on zeolites or cationic or anionic resins (FR-A-2.510.581), a stage of ultrafiltration of maltose syrups (U.S. Pat. No. 4.429.122), the combined use of several different enzymes, that is to say an α-amylase, a β-amylase and an isoamylase or a pullulanase (FR-A2.012.831).

This last technique presents, in relation to the preceding ones, numerous advantages. It suffers nevertheless from certain disadvantages, including in particular the one residing in the fact that the saccharifications have to be carried out with very low levels of dry matter, of the order of 20 g/1, in order to obtain a maximum hydrolysis efficiency of the enzymes.

The document FR-A-2.000.580 describes a method of preparing a syrup with a high content of maltitol by hydrogenation of a syrup with a high content of maltose which is obtained by liquefaction of a starch milk with a low content of dry matter to a dextrose equivalent lower than 2, the product thus obtained being saccharified under the action of specific enzymes.

This process is expensive, gives a mediocre yield and gives rise to problems of bacterial contamination and to occurrences of retrogradation of the amylose. In addition, the syrup obtained contains proportions of polymers with a degree of polymerization (DP in the rest of the specification) greater than or equal to 4, which are a nuisance.

More recently, the document U.S. Pat. No. 5.141.859 proposed a method of manufacturing a syrup with a high maltose content, using two successive stages of saccharification. This document advocates in fact a method comprising a first stage of saccharification in the presence of a β-amylase and a subsequent stage of saccharification in the presence of a maltogenic α-amylase. According to this document, the maltogenic α-amylase is used, after the first stage of saccharification with the β-amylase, to hydrolyse the oligosaccharides (from DP3 to DP7), and essentially the maltotriose (trisaccharide) into maltose and glucose.

In a surprising and unexpected manner, the applicant company has noted that syrups with a maltose content as high as those described in the document U.S. Pat. No. 5.141.859 could be obtained by saccharifying a starch milk which had first been liquefied by means of a maltogenic α-amylase, then in continuing this saccharification by means of a β-amylase.

Thus, contrary to the teaching of the document U.S. Pat. No. A5.141.859, the applicant company has revealed that the maltogenic α-amylase was capable of hydrolysing the polysaccharides of a liquefied starch milk, and that this enzyme could thus be used directly on the latter without first of all going through a stage of saccharification with the β-amylase.

This discovery is all the more surprising since it would have been possible to think that, after the saccharification with the aid of a maltogenic α-amylase, continuing the saccharification with the β-amylase would not have any effect on the high maltose content of the syrup obtained. In fact, maltogenic α-amylase is known, on the one hand, for releasing the α-maltose and, on the other hand, for being capable of hydrolysing, unlike the β-amylase, the maltotriose into maltose and glucose. It could therefore be expected that the use of the maltogenic α-amylase would, on its own, have made it possible to obtain a hydrolysate with a very high maltose content and that the subsequent addition of β-amylase was superfluous. The applicant company established, against all expectation, that such was not the case.

The invention thus proposes a method of manufacturing a maltose-rich syrup, comprising the successive stages, consisting of:

(a) carrying out a liquefaction of a starch milk;
(b) carrying out a saccharification of the liquefied starch milk in the presence of a maltogenic α-amylase;
(c) continuing the saccharification of the liquefied starch milk in the presence of a β-amylase and at least one debranching enzyme chosen from the group consisting of pullulanases and isoamylases with a view to obtaining a syrup which is rich in maltose.

The invention proposes in addition a method of manufacturing a maltose-rich syrup, comprising the successive stages, consisting of:

(a) carrying out a liquefaction of the starch milk;
(b) carrying out a saccharification of the liquefied starch milk in the presence of a maltogenic α-amylase and at least one debranching enzyme chosen from the group consisting of pullulanases and isoamylases with a view to obtaining a syrup which is rich in maltose.

If necessary, stage (b) of saccharification of the liquefied starch milk can be continued in the presence of a β-amylase.

In pursuing its research efforts into the characteristics of maltogenic α-amylase, the applicant company has, in addition, established that if the use of maltogenic α-amylase made it possible, effectively and advantageously, to lower the proportion of maltotriose by hydrolysis of the latter into maltose and glucose, it presented the major disadvantage of generating significant quantities of glucose, and possibly of sorbitol in the case of hydrogenation of the hydrolysates. Indeed, to the residual glucose obtained after saccharification of the liquefied starch milk is added a significant proportion of glucose stemming from the hydrolysis of the maltotriose by the maltogenic α-amylase.

These significant quantities of glucose, and thus of sorbitol after hydrogenation, make the crystallisation of the maltitol more difficult and lead to a drop in the richness of the crystals, making them poorly suited to certain applications such as the manufacture of chocolate, for example.

In addition, the persistence of free glucose or sorbitol in the maltose or maltitol syrups causes other disadvantages such as a drop in the viscosity and the relative humidity balance of the products into which they are incorporated as sugar substitutes.

Conscious that there exists a growing interest in products with a very high maltose content, the applicant company has conducted extensive research with the aim of perfecting an economic and extremely reliable method making it possible to obtain such products.

In a manner which was extremely simple and particularly effective in view of everything previously proposed, the applicant company established that syrups with a very high maltose content could easily be manufactured by submitting a maltose syrup, obtained in accordance with the method according to the invention, to a supplementary stage of transformation of the glucose with the aid in particular of a glucose oxidase, of a raising agent or of an oxidising bacterium.

Despite its simplicity, this supplementary stage of the method according to the invention makes it surprisingly possible to manufacture, with an excellent yield, a syrup with a very high maltose content without having recourse to an expensive separation stage, using chromatography for example, such as is the case with documents EP-A-185.595 and U.S. Pat. No. 5,141,859.

The first stage of the method according to the invention is itself known. It consists in liquefying a starch milk, which can be of any botanical origin: it can come from corn, from maize or from potato, for example.

This starch or potato flour milk has acid added to it in the case of liquefaction termed acid, or has an α-amylase added to it in the case of enzymatic liquefaction.

In the method according to the invention, it is preferred that careful hydrolysis of the starch milk is carried out in such a way as to obtain a liquefied starch milk with a low transformation rate. Thus, the conditions of temperature, of pH, of levels of enzyme and of calcium, known to the expert, are determined in a manner such that they make it possible to obtain a DE (Dextrose Equivalent) lower than 10, preferably lower than 6, and more particularly lower than 4.

By preference, the liquefaction stage is carried out in two sub-stages, the first consisting of heating up, for several minutes and at a temperature of between 105 and 108° C., the starch milk in the presence of an α-amylase (type: TERMAMYL$^R$ 120L marketed by the firm NOVO) and a calcium-based activator, the second consisting in heating the starch milk thus treated to a temperature of between 95 and 100° C. for one to two hours.

Once the liquefaction stage is completed, in the conditions of content of dry matter, of pH, of enzyme and calcium levels well known to the expert, the next step is the inhibition of the α-amylase. This inhibition of the α-amylase can preferably be done by means of heat, by proceeding, after the liquefaction, to a thermal shock lasting several seconds at a temperature greater than or equal to 130° C.

Then the saccharification stage is carried out. During this stage, the liquefied starch milk is first subjected to the action of a maltogenic α-amylase, such as the one marketed by the firm NOVO, under the name of Maltogenase$^R$. During this first saccharification stage, the maltogenic α-amylase can be added all at once or in several phases.

Then, after having let the maltogenic α-amylase act, the next step is the saccharification of the liquefied starch milk by means of a β-amylase such as that marketed by the firm GENENCOR under the designation SPEZYME$^R$ BBA 1500.

During these stages, it is advisable to associate with the enzymes having a maltogenic activity (maltogenic α-amylase and β-amylase) an enzyme which specifically hydrolyses the α-1,6 bonds of the starch. This addition of a debranching enzyme makes it possible on the one hand to accelerate the hydrolysis reactions without simultaneously accelerating the reversion reactions and, on the other hand, to reduce the quantity of highly branched oligosaccharides generally resisting the action of the maltogenic enzymes.

This addition of a debranching enzyme can be done, in the method according to the invention, at the moment of adding the maltogenic α-amylase or at the moment of adding the β-amylase.

The applicant company has noted that if a debranching enzyme is added at the moment of adding the maltogenic α-amylase, it is possible not to use the β-amylase to continue with the stage of saccharification of the liquefied starch milk.

According to the invention, the debranching enzyme is chosen from the group formed by pullulanases and isoamylases.

The pullulanase is, for example, the one marketed by the firm ABM under the designation PULLUZYME$^R$.

The isoamylase is, for example, the one marketed by the firm HAYASHIBARA.

Advantageously, the method according to the invention is used in the presence of isoamylase, about which the applicant company noticed that it made it possible to obtain a maltose syrup presenting a higher maltose content than by using a pullulanase.

In a particular embodiment of the invention, the saccharification stage can be equally carried out totally or partially in the presence of fungic α-amylase.

At the end of saccharification, it is possible to add a little α-amylase and this generally improves the subsequent filtration stages. The quantities and the conditions of action of the different enzymes used in the stages of liquefaction and saccharification of the starch milk are generally those which are recommended for the hydrolysis of starch and are well known to the person skilled in the art.

Saccharification is carried out until the hydrolysate of maltose contains at least 87% by weight of maltose and, by preference, about 90% by weight of maltose. It lasts about 72 hours.

The hydrolysate thus saccharified is then filtered on a precoat filter or by microfiltration on membranes, then demineralised.

At this stage of the method according to the invention, it would be possible to carry out on this saccharified and purified hydrolysate, crystallisation of the maltose or molecular sieving, this molecular sieving making it possible to enrich the hydrolysate with maltose. This stage of molecular sieving can make it possible thus to recover:

either a first fraction enriched with maltose and higher oligosaccharides and a second fraction enriched with glucose;

or a first fraction enriched with higher oligosaccharides and a second fraction enriched with maltose and glucose or, finally, a first fraction enriched with higher oligosaccharides, a second fraction enriched with maltose, and a third fraction enriched with glucose.

This stage of molecular sieving can consist, for example, in a stage of chromatographic separation or in a stage of separation on membranes.

The stage of chromatographic fractionation is carried out in a manner which is itself known, either discontinuously or continuously (simulated moving bed), on adsorbents such as cationic resins, or on very strongly acid zeolites, preferably charged with the aid of alkaline ions or alkaline earth ions such as calcium or magnesium, but more preferably with the aid of sodium ions.

Instead of and in the place of the stage of chromatographic separation, it is possible, in the method according to the invention, to use a stage of separation by nanofiltration on membranes. Membranes with different diameters of pore are manufactured from numerous polymers and copolymers such as polysulfones, polyamides, polyacrylonitrates, polycarbonates, polyfurans etc.

Examples of the use of such membranes are described in particular in the documents U.S. Pat. No. 4.511.654, U.S. Pat. No. 4.429.122 and WO-A-95/10627.

According to an advantageous embodiment of the method according to the invention, the non-maltose portion coming from the membranes or the chromatography, comprising the fraction enriched with glucose and/or the fraction enriched with higher oligosaccharides, is recycled upstream of the saccharification stage.

The hydrolysate (or maltose syrup), thus obtained, can then be submitted to a supplementary stage of transformation of the glucose followed by a stage of basification on an anionic exchanger. This supplementary stage can be carried out by enzymatic oxidation or with the aid of an oxidising bacterium. It can also be carried out with the aid of raising agents which transform the glucose into alcohol which is eliminated by evaporation later on in the process.

A crude enzymatic composition of glucose oxidase, which also contains catalase, is preferably used for the enzymatic oxidation.

The glucose oxidase catalyses the following reaction:

$$Glucose + O_2 + H_2O \rightarrow GLUCONIC\ ACID + H_2O_2$$

The catalase transforms the oxygenated water thus produced according to the reaction:

$$H_2O_2 \rightarrow H_2O + 1/2 O_2$$

An enzymatic composition of this sort is available, for example, from the firm NOVO, DENMARK under the designation NOVOZYM 771.

In a preferred embodiment of the method according to the invention, the glucose oxidase used in the stage of enzymatic oxidation is purified and, in particular, freed of its contaminating amyloglucosidase activity.

A glucose oxidase of this sort is available, for example, from the firm FRIMOND under the designation FRIMOX.

This enzymatic oxidation should take place in an aerated medium and the pH of such a medium is preferably kept at a value of between 3.5 and 8.0, by preference between 4.0 and 7.0, and even more preferably between 5.0 and 6.0.

The maltose concentration in the hydrolysate is not critical and can vary from 5 to 75%. However, raised concentrations in the hydrolysate make it necessary to work by regulating the pH with aid of a base or by carrying out the oxidation in the presence of a buffer salt such as calcium carbonate. For reasons of economy, however, carrying out the oxidation on aqueous solutions containing about 30 to 50% of dry matter is preferred.

The temperature can be adjusted in a wide range varying from 15 to 70° C. but, for reasons of convenience, working at around 30–40° C. is preferred, temperatures at which the enzyme shows itself to be more stable.

A convenient material which makes it possible to carry out this oxidation consists of an aerobic fermenter, although it is not at all necessary for this stage to take place in conditions that are sterile nor even rigorously aseptic. The quantity of enzymes used is such that the oxidation takes place in 0.5 to 24 hours.

When a raising agent is used in the method according to the invention to transform the residual glucose, said agent belongs, for example, to the genus Saccaromyces.

When the supplementary stage of transforming the residual glucose by means of an oxidising bacterium, the latter is chosen from the group consisting of Serratia, Pseudonomas, Gluconobacter, Acetobacter and Aspergillus.

As far as the second stage of basification is concerned, the preferred anionic exchanger to use is a strong anionic resin which makes it possible to fix effectively the weak acids such as the gluconic acid or other acid oxidation products of the glucose which could appear particularly when this resin is heated up to a high temperature.

The preferred resins are those which have functional groups of the quaternary amine type and even more preferably quaternary trimethyl amine groups such as the resin AMBERLITE IRA 900 marketed by ROHM and HAAS.

These resins are used in their hydroxyl or strong "OH" base form.

To increase their regeneration yield with the alkali, they can by preference be coupled with a weak anionic resin, essentially carrying tertiary amino groups, such as AMBERLITE IRA 93 from the same company.

Thanks to the method according to the invention which profits from the benefits obtained simultaneously from the hydrolysis stages used and from the oxidation and basification stages, it is possible to obtain, with yields greater than 90%, a hydrolysate of starch of which the maltose content is greater than 95%, and even greater than 98% when an isoamylase is used in the hydrolysis stages.

The maltose hydrolysate obtained according to the method of the invention can then be hydrogenated catalytically.

The hydrogenation of such a hydrolysate is carried out in accordance with the rules of the art, which lead, for example, to the production of sorbitol from glucose.

For this stage, catalysts based on ruthenium can be used just as well as RANEY nickel catalysts. However, the use of the less expensive RANEY nickel catalysts is preferred.

In practice, between 1 and 10% by weight of catalyst in relation to the dry matter of the hydrolysate subjected to hydrogenation is used. The hydrogenation is carried out by preference on a hydrolysate, the dry matter of which is between 15 and 50%, in practice around 30 to 45%, with a hydrogen pressure of between 20 and 200 bar. It can be carried out either continuously or discontinuously.

When the process is discontinuous, the hydrogen pressure used is generally between 30 and 60 bar and the temperature at which the hydrogenation takes place is between 100 and 150° C. Care is also taken to maintain the pH of the hydrogenation medium by the addition of soda or of carbonate of soda, for example, but without exceeding a pH of 9.0. This way of working makes it possible to avoid any cracking or isomerisation products appearing.

The reaction is stopped when the content of reducing sugars in the reaction medium has become lower than 1 %, by preference even lower than 0.5% and more particularly lower than 0.1%.

After cooling the reaction medium, the catalyst is eliminated by filtration and the maltitol syrup thus obtained is demineralised on cationic and anionic resins. At this stage, the syrups contain at least 85% maltitol.

According to a first variation of the method according to the invention, there is carried out on the maltitol syrup obtained in the preceding hydrogenation stage, the succession of stages, itself known (for example from document EP-A-189.704), consisting in:

carrying out a chromatographic fractionation, itself known, in such a way as to obtain a fraction rich in maltitol;

concentrating the maltitol-rich fraction;

crystallising and separating the maltitol crystals formed;

recycling the crystallisation mother liquors upstream of the stage of chromatographic fractionation.

Such a succession of stages makes it possible to increase the specific yields of crystallisation.

According to a second variation of the method according to the invention, there is carried out on the maltitol syrup obtained in the preceding hydrogenation stage, the succession of the following stages, consisting in:

concentrating the maltitol syrup;

crystallising and separating the maltitol crystals formed;

carrying out on the crystallisation mother liquors a chromatographic fractionation in such a way as to obtain a fraction which is enriched with maltitol and a fraction which is depleted in maltitol;

recycling the fraction which is enriched with maltitol, upstream of the crystallisation stage;

possibly carrying out on the fraction which is depleted in maltitol, either an acidic hydrolysis, or an enzymatic hydrolysis by means of, for example, an amyloglucosidase, immobilised or not;

possibly hydrogenating the hydrolysate obtained in order to transform it into a sorbitol syrup.

According to another variation of the method according to the invention, there is carried out on the maltose hydrolysate obtained after saccharification the succession of the following stages, consisting in:

possibly carrying out a chromatographic fractionation, itself known, in such a way as to obtain a fraction which is rich in maltose and more or less rich in maltotriose;

hydrogenating the maltose-rich fraction;

crystallising and separating the maltitol crystals formed.

Other characteristics and advantages of the invention will appear clearly in reading the following examples. They are, however, given only by way of non-restrictive example.

EXAMPLE 1

A starch milk, with 31% dry matter, is liquefied in standard fashion with the aid of 0.2% TERMAMYL$^R$ 120L (α-amylase marketed by the firm NOVO) to a pH of 5.7 to 6.5 up to a DE slightly below 4.

Then the reaction medium is heated for a few seconds at 140° C. so as to inhibit the α-amylase, then the pH is adjusted between 5 and 5.5 and the temperature adjusted to 55° C.

The saccharification is carried out to a dry matter of 25%, or slightly less, first of all in the presence of pullulanase (PULLUZYME$^R$ 750L marketed by the firm ABM) and of maltogenic (α-amylase (MALTOGENASE$^R$ 4000L marketed by the firm NOVO) at respective doses of 0.1% and 0.3% of the dry matter After approximately 48 hours of saccharification, but in any case, once the maltose content reaches or exceeds 75%, 0.05% of SPEZYME$^R$ DBA (marketed by the firm GENENCOR) is added. The saccharification, which lasts about 72 hours, produces a hydrolysate showing the following composition—glucose: 6.6%, maltose: 86.0%, DP3: 1.6%, DP4: 3.5%, DP5 and +: 2.3%.

The hydrolysate then undergoes standard purification by filtration, decoloration and demineralisation, then is concentrated to approximately 30% dry matter.

EXAMPLE 2

Exactly the same stages of liquefaction and of saccharification as those described in example 1 above are carried out on a starch milk, except for the fact that, during the saccharification, an isoamylase is used, and that the pH is kept at 4.7 during the first 48 hours.

The maltose hydrolysate obtained, at the end of 72 hours, shows the following composition—glucose: 7.2%, maltose: 88.2%, DP3: 2.2%, DP4 and +: 2.4%.

EXAMPLE 3

Exactly the same stages of liquefaction and of saccharification as those described in example 1 above are carried out on a starch milk, except that the saccharification is begun with Maltogenase$^R$ alone, and that after 48 hours SPEZYME$^R$ DBA and PULLUZYME$^R$ 750L are added.

The maltose hydrolysate obtained at the end of 72 hours shows the following composition—glucose: 6.3%, maltose: 84.1%, DP3: 1.8%, DP4 2.6%, DP5 and +: 5.2%

EXAMPLE 4

The solution with 30% maltose hydrolysate obtained in example 1 above is submitted to the action of the glucose oxidase in a ratio of 0.7%° FRIMOX (marketed by the firm FRIMOND) of the dry matter in the presence of 4.8 %° catalase (marketed by the firm BOEHRINGER) of the dry matter.

This reaction takes place in an aerated vat with a ratio of 1.5 volume of air per volume of solution and per minute at a controlled pH of 6.0 by the progressive addition of soda.

It takes place at 35° over 7 hours, at the end of which the glucose content is lower than 0.5%.

This solution is then treated on a battery of resins for ion exchange, containing in series a strong cationic resin IR200C then a strong anionic resin IRA900. This demineralisation is brought to an end when the resistivity of the solution has fallen to a value lower than 10,000 ohms-cm.

The hydrolysate then shows the following composition —glucose: 0.5%, maltose: 91.6%, DP3: 1.7%, DP4 3.7%, DP5 and +: 2.4%.

EXAMPLE 5

Exactly the same succession of stages as those described in example 4 above is carried out on a solution with 30% maltose hydrolysate.

The hydrolysate then shows the following composition —glucose 0.3%, maltose: 94.7%, DP3: 2.4%, DP4 and +: 2.6%.

EXAMPLE 6

The maltose hydrolysate of example 3 is placed in an aerobic reactor at 30° C. Some ammonia is added (in 20% concentration), in a ratio of 2.7ml/litre of medium, of which 75% are added immediately and the remaining 25% after approximately one hour of reaction. The medium is stirred at 750 rpm, aerated at 1.2 vvm and has 3.3 g/l of raising agents (SAF-INSTANT marketed by S.I. LESAFFRE) added to it.

After approximately 12 hours of reaction, the composition obtained is the following —glucose: 0.5%, maltose: 89.3%, DP3: 1.9%, DP4: 2.8%, DP5 and +5.5%.

EXAMPLE 7

*Serratia Marcescens* is preserved in the form of a frozen tube. One tube serves to seed 1.5 l of preculture medium containing 50 g/l glucose, 7 g/l extract of raising agent, 5 g/l corn steep and 5 g/l calcium carbonate. This preculture is put to incubate for 24 h at 30° C.

It is then used to seed 15 l of culture medium containing the maltose hydrolysate obtained in example 3 (approximately 130 g/l maltose and 10 g/l glucose), 4 g/l ammonium phosphate, 0.4 g/l magnesium sulphate, 0.1 g/l iron sulphate and 10 g/l calcium carbonate. The culture is carried out at 32° C. with stirring at 700 rpm and an aeration of 1 vvm (15 litres of air per minute).

In these conditions, the glucose is entirely consumed in 8 h of culture (transformed into gluconic and 2-ketogluconic acid) without reducing the maltose content.

EXAMPLE 8

The maltose hydrolysate obtained in example 1 above is submitted to a stage of crystallisation of the maltose in the following manner. A maltose solution in a strength of 75% by weight is prepared at a temperature of 75° C. The maltose is seeded with 5% by weight germs of maltose crystals and the solution cooled from 75° C. to 40° C., at a ratio of 0.5° C. per hour, stirring the solution at 50 rpm in a crystalliser with a double wall.

At the end of crystallisation, the crystals are separated from the mother liquid with the aid of a conventional centrifugal dryer.

The crystallisation yield is 50% by weight expressed in weight of crystallised maltose over the initial weight of maltose. The purity of maltose of the crystals recuperated is 97.5% of the dry matter. The water content is 5%.

EXAMPLE 9

The next step is a stage of continuous chromatography of the maltose hydrolysate such as obtained in example 1 above, in the following manner.

4 columns of a litre of sodic resin PCR 732 thermostatted at 75° C. are assembled in series and supplied continuously with the maltose hydrolysate brought to a strength of 60% by weight, with a flow rate of 110 ml/l.

As they leave the column, the fractions enriched with maltose are recovered and have the following composition—glucose : 6%, maltose: 91.2%, DP3 0.6%, DP higher 2.2%.

The chromatographic yield of maltose is 91.5%.

What is claimed is:

1. Method of manufacturing a maltose-rich syrup having a maltose content greater than 87%, consisting of the successive stages of:

(a) carrying out a liquefaction of a starch milk using an α-amylase;
   (b) inhibiting the action of the α-amylase;
   (c) first carrying out a saccharification of the liquefied starch milk in the presence of a maltogenic α-amylase until the maltose content reaches or exceeds 75%;
   (d) then continuing the saccharification in the presence of a β-amylase and at least one debranching enzyme selected from the group consisting of pullulanases and isoamylases, so as to obtain a syrup having a maltose content greater than 87%.

2. Method according to claim 1, wherein the saccharification in the presence of the maltogenic α-amylase is carried out for a period of about 48 hours.

3. Method according to claim 1, wherein the saccharification in the presence of the β-amylase is carried out until the maltose syrup contains at least 90% by weight of maltose.

4. Method according to claim 3, wherein the saccharification in the presence of the β-amylase is carried out until the maltose syrup contains at least 95% by weight of maltose.

5. Method according to claim 1, wherein the maltose syrup is subjected to a supplementary stage of transformation of the glucose present in the syrup by an agent selected from the group consisting of glucose oxidase, yeast and an oxidizing bacterium.

6. method according to claim 5, wherein the glucose oxidase is purified.

7. Method according to claim 1, wherein the inhibition of the α-amylase is carried out by a thermal shock at a temperature greater than or equal to 130° C.

8. Method of manufacturing a maltitol-rich syrup having a maltitol content greater than 87%, by hydrogenation of a maltose-rich syrup, wherein the maltose-rich syrup is obtained by the method according to claim 1.

9. Method of manufacturing a maltitol-rich syrup according to claim 8 wherein a further step of chromatographic fractionation is carried out in such a manner as to obtain a maltitol-rich fraction and a maltitol-depleted fraction.

10. Method of manufacturing a maltitol-rich syrup according to claim 9, wherein said maltitol-depleted fraction is subjected to acid or enzymatic hydrolysis, and the hydrolysate thus obtained is hydrogenated in order to obtain a sorbitol syrup.

* * * * *